| United States Patent [19] | [11] Patent Number: 4,992,571 |
|---|---|
| Fukuyama et al. | [45] Date of Patent: Feb. 12, 1991 |

[54] METHOD FOR MAKING OCTYLOXY SUBSTITUTED DIPHENYL IODONIUM HEXAFLUORO METALLOID SALTS

[75] Inventors: James M. Fukuyama, Clifton Park; Julia L. Lee, Schenectady; James V. Crivello, Clifton Park, all of N.Y.

[73] Assignee: General Electric Company, Schenectady, N.Y.

[21] Appl. No.: 429,744

[22] Filed: Oct. 31, 1989

[51] Int. Cl.$^5$ .................................................. C07F 9/90
[52] U.S. Cl. ........................................... 556/64; 556/1
[58] Field of Search ............................ 556/64, 1, 13

[56] References Cited

U.S. PATENT DOCUMENTS

| 4,058,400 | 11/1977 | Crivello | 556/1 X |
|---|---|---|---|
| 4,310,469 | 1/1982 | Crivello | 556/1 X |
| 4,399,071 | 8/1983 | Crivello et al. | 556/64 |
| 4,537,725 | 8/1985 | Irving | 556/64 X |
| 4,933,377 | 6/1990 | Saeva et al. | 556/64 X |

*Primary Examiner*—Arthur C. Prescott
*Attorney, Agent, or Firm*—William A. Teoli; James C. Davis, Jr.; William H. Pittman

[57] ABSTRACT

A one pot method is provided for preparing an (octyloxyphenyl) phenyliodonium tosylate and the corresponding hexafluorometalloid salt. n-Octylphenyl ether is initially prepared using a halooctane and phenol in the presence of a phase transfer catalyst followed by the addition of iodobenzene, a peracid, and p-toluene sulfonic acid. The resulting (octyloxyphenyl)phenyl iodonium tosylate can be directly metathesized after an optional treatment step with an alkali metal hexafluoroantimonate salt. The (octyloxyphenyl) iodonium hexafluorometalloid salt can be used as a photoinitiator for UV curable organic materials such as epoxy resins.

6 Claims, No Drawings 4,992,571

METHOD FOR MAKING OCTYLOXY SUBSTITUTED DIPHENYL IODONIUM HEXAFLUORO METALLOID SALTS

CROSS REFERENCE TO RELATED APPLICATIONS

Reference is made to copending application Crivello et al, Ser. No. 171,063, filed 3/21/1988 for NON-TOXIC ARYL ONIUM SALTS, UV CURABLE COATING COMPOSITIONS AND FOOD PACKAGING USE which is assigned to the same assignee as the present invention and incorporated herein by reference

BACKGROUND OF THE INVENTION

Prior to the present invention, as shown by Crivello, U.S. Pat. No. 3,981,897, Method for Making Certain Halonium Salt Photoinitiators, diaryliodonium salts, such as diphenyliodonium hexafluoroantimonate were prepared by effecting reaction between an intermediate diarylhalonium bisulfate and an alkylhexafluoro salt, such as diphenyliodonium hexafluoroantimonate.

In copending application Ser. No. 171,063, filed 3/21/1988, a step-wise procedure is shown for making an (octyloxyphenyl) phenyliodonium hexafluorometalloid salt which is used as a photoinitiator in non-toxic UV curable coating compositions. The procedure of Ser. No. 171,063 is directed to the initial synthesis of n-octylphenylether and the separate synthesis of a phenyliodosotosylate. The (octyloxyphenyl) phenyliodonium tosylate is synthesized in a separate reaction. Finally, the (octyloxyphenyl) phenyliodonium tosylate is metathasized with sodium hexafluoroantimonate to provide the desired (octyloxyphenyl) phenyliodonium hexafluoroantimonate salt. Although the method of Ser. No. 171,063 can provide the preferred (4-octyloxyphenyl) phenyliodonium hexafluoroantimonate salt at satisfactory yields, several steps are required which renders the procedure unsuitable for commercial production.

SUMMARY OF THE INVENTION

The present invention is based on the discovery that (octyloxyphenyl) phenyliodonium hexafluoroantimonate can be made by a one pot procedure involving the employment of a phase transfer catalyst in the initial synthesis of the n-octylphenyl ether, followed by the removal of the aqueous basic solution from the initial synthesis mixture. Phenyl iodide and a peracid can be added directly to the n-octylphenyl ether followed by the addition of p-toluene sulfonic acid in the same reaction vessel. The resulting hydroxy (tosyloxy) iodobenzene which forms, reacts in situ with the n-octylphenyl ether while the temperature is maintained at about 30° C. or below. Recovery of the resulting (octyloxyphenyl) phenyliodonium tosylate can be achieved by extracting the reaction mixture with an organic solvent and water and triturating the reaction mixture with aliphatic hydrocarbon solvent. The metathesis of the (octyloxyphenyl) phenyliodonium tosylate and an alkali metal hexafluoroantimonate salt can be effected in the same vessel. As used hereinafter the term "(octyloxyphenyl) phenyliodonium hexafluorometalloid salt" means the corresponding hexafluoroantimonate, hexafluorophosphate, or hexafluoroarsenate salt.

STATEMENT OF THE INVENTION

There is provided by the present invention, a one pot method for making an (octyloxyphenyl) phenyliodonium hexafluorometalloid salt which comprises, (1) effecting reaction between phenol and a-bromo octane in the presence of an aqueous basic solution and a phase transfer catalyst to form n-octylphenyl ether, (2) effecting the removal of the aqueous basic solution from the mixture of (1), (3) adding with agitation to the mixture of (2), iodobenzene, a peracid and a toluenesulfonic acid, while maintaining the resulting mixture at a temperature of from −20° C. to 100° C. to form an (octyloxyphenyl) phenyliodonium tosylate complex, (4) effecting the separation of the (octyloxyphenyl) phenyliodonium tosylate from the complex of (3) and, (5) effecting a metathesis reaction between the (octyloxyphenyl) phenyliodonium tosylate of (4) and an alkali metal hexafluorometalloid salt to form the (octyloxyphenyl) phenyliodonium hexafluorometalloid salt.

In the practice of the method of the present invention, n-octylphenyl ether is initially synthesized by effecting reaction between 1 to 3 mols of phenol, per mol of a halooctane such as 1-bromooctane in the presence of a phase transfer catalyst, for example tetrabutylammoniumbromide, cetylammonium chloride, and trimethylbenzylammonium chloride, an inert organic solvent, for example, toluene, benzene, xylene, chlorobenzene, n-hexane, n-heptane, n-octane, dichloromethane, and an aqueous alkali metal hydroxide solution, such as sodium or potassium hydroxide. The reaction mixture can be agitated and refluxed for a period of from 3 to 36 hours and then allowed to cool to room temperature. The aqueous layer can be removed by decantation and the organic layer can be extracted with an alkali metal hydroxide solution with water thereafter the organic solvent can be removed under reduced pressure. Iodobenzene can be added to the same pot containing the n-octylphenyl ether in substantially equal molar amounts at temperatures in a range of from 0° C. to 60° C. A suitable peracid, such as peracetic acid, perbenzoic acid, m-chloroperbenzoic, or perphthalic acid can be added gradually to the resulting mixture of iodobenzene and n-octylphenyl ether while it is being stirred and maintained at a temperature of 20° C. to 40° C. over a period of from 15 to 120 minutes. After the peracid has been added, the reaction mixture can be agitated for an additional 1 to 30 hours. A toluenesulfonic acid, such as p-toluenesulfonic acid can then be added to the mixture which can be agitated for an additional 1 to 8 hours. The heterogeneous reaction mixture then can become homogeneous, and the mixture can turn orange after a short period of time.

Various workup procedures can be used to recover the (octyloxyphenyl) phenyliodonium tosylate from the reaction mixture prior to the addition of the alkali metal hexafluorometalloid salt. One procedure involves the addition of an inert organic solvent, such as toluene and water to the reaction mixture while it is agitated, followed by the separation of the aqueous layer and extraction thereof with an inert organic solvent. The organic solvent extract can be combined with the original organic phase. The organic solvent layer can then be extracted once with water followed by treatment with an aliphatic hydrocarbon solvent, such as n-heptane or n-octane to effect the precipitation of the desired tosylate product which can be an off-white solid.

Another procedure which can be used to recover the (octyloxyphenyl) phenyliodonium tosylate is triturating the reaction mixture with an aliphatic hydrocarbon, such as heptane followed by decanting the aliphatic hydrocarbon from the resulting orange oil. A second trituration with the aliphatic hydrocarbon can be used followed by triturating with water at least twice. The resulting solvent can then be triturated once more with the aliphatic hydrocarbon and thereafter filtered and washed.

An additional work-up procedure which can be employed to recover the (octyloxyphenyl) phenyliodonium tosylate product is to initially add with stirring an inert aromatic organic solvent, such as toluene, to the reaction mixture with an equal volume of water followed by separating the aqueous layer and extracting it once with the aromatic organic solvent. The tosylate product can then be extracted once with water; thereafter the solvent can be removed under reduced pressure resulting in an orange solid. The orange solid can be broken up and triturated with the aliphatic organic solvent, such as heptane, filtered and washed again with the aliphatic organic solvent.

The metathesis reaction can be effected with a mixture of an inert organic solvent, such as acetone and an alkali metal hexafluorometalloid salt, such as the corresponding hexafluoroantimonate, hexafluorophosphate or hexafluoroarensate, referred to hereinafter as the hexafluoroantimonate salt. The hexafluoroantimonate salt can be added to the (octyloxyphenyl) phenyliodonium tosylate followed by agitating the resulting mixture for a period of from 15 to 180 minutes. The mixture can then be filtered and then added to an excess amount of distilled water. The resulting oil can then be triturated with water and the water decanted followed by the addition of further amounts of water. The mixture can then be stirred for another 15 to 180 minutes and the water decanted and an inert aliphatic solvent such as n-heptane or n-octane can be added. This procedure results in the crystallization of the solid (octyloxyphenyl) phenyliodonium hexafluoroantimonate which can be broken up, washed with additional aliphatic organic solvent and then filtered.

In order that those skilled in the art will be better able to practice the present invention the following example is given by way of illustration and not by way of limitation. All parts are by weight unless otherwise indicated.

EXAMPLE

A mixture of 10.70 grams (liquified, 88%) phenol, (0.10 mol), 0.44 grams (33.0 mmol) of 1-bromooctane, 5 ml of toluene, 1.66 grams (5.0 mmol) of tetrabutylammonium bromide, 10 ml of water and 12.5 grams of a 40% solution (0.10 mol) of potassium hydroxide, was heated to reflux for a period of 18 hours with stirring. The reaction was then cooled to room temperature and the aqueous layer was removed. The organic layer was extracted once with 0.5N KOH (20 ml) once with water (20 ml). The toluene was removed under reduced pressure and the n-octylphenyl ether carried on without additional purification.

There was added 6.8 grams (33.0 mmol) of iodobenzene to the n-octylphenylether which was being stirred while the mixture was maintained at room temperature. There were then added dropwise, 19.5 grams (0.08 mol) of 32% peracetic acid to the mixture, while it was being stirred and maintained at a temperature of about 30° C. Following the addition of the peracetic acid, the reaction mixture was allowed to stir for 15 hours resulting in the formation of a precipitate. There were then added 10.0 grams, (0.053 mol) of p-toluenesulfonic acid and the resulting reaction mixture was stirred for an additional 4 hours. The resulting mixture became homogeneous after a short period of time.

The reaction mixture was triturated twice with 70 ml of water and once with 70 ml of n-heptane. After each wash the solvent was filtered from the solid product. It was then added to the resulting mixture 60 ml of acetone and 9.4 grams of sodium hexafluoroantimonate while the mixture was stirred for an additional 30 minute period. The acetone solution was then filtered and the acetone mixture was added to 500 ml of distilled water. There was obtained an oil which was triturated for 5 minutes and the water was decanted and 200 ml of fresh water was added. After stirring for another 5 minutes, the water was decanted and 200 ml of heptane was added. The material crystallized and the solid mass was broken up, triturated with heptane and then filtered. There was obtained a 82% yield of (4-octyloxyphenyl) phenyliodonium hexafluoroantimonate.

The (4-octyloxyphenyl) phenyliodonium hexafluoroantimonate salt is found to be useful as a photo initiator for 4-vinylcyclohexene dioxide when employed at about 3% by weight using a GEH3T7 lamp at a distance of 6 inches at an exposure of about 1 second.

Although the above example is directed to only a few of the very many variables which can be used in the practice of the method of the present invention, it should be understood that the present invention is directed to the employment of a much broader variety of the agents in conditions as set forth in the description preceding this example.

What is claimed is:

1. A one pot method for making an (octyloxyphenyl) phenyliodonium hexafluorometalloid salt which comprises,
    (1) effecting reaction between phenol and 1-bromo octane in the presence of an aqueous basic solution and a phase transfer catalyst to form n-octylphenyl ether,
    (2) effecting the removal of the aqueous basic solution from the mixture of (1),
    (3) adding with agitation to the mixture of (2), iodobenzene, peracid and a toluenesulfonic acid while maintaining the resulting mixture at a temperature of from 20° C. to 100° C. to form an (octyloxyphenyl) phenyliodonium tosylate complex,
    (4) effecting the separation of the (octyloxyphenyl) phenyliodonium tosylate from the complex of (3) and,
    (5) effecting a metathesis reaction between the (octyloxyphenyl) phenyliodonium tosylate of (4) and an alkali metal hexafluorometalloid salt to form the (octyloxyphenyl) phenyliodonium hexafluorometalloid salt.

2. A method in accordance with claim 1, where the (octyloxyphenyl) phenyliodonium hexafluorometalloid salt is (4-octyloxyphenyl) phenyliodonium hexafluoroantimonate.

3. A method in accordance with claim 1, where the phase transfer catalyst in step 1 is tetrabutylammonium bromide.

4. A method in accordance with claim 1, where the peracid in step 3 is peracetic acid.

5. A method in accordance with claim 1, where the octyloxyphenyl phenyliodonium tosylate is separated from the complex by initially adding an aromatic organic solvent in water to the complex followed by separation of the aqueous layer and extraction with the aromatic organic solvent and the trituration of the solid residue with n-octane.

6. A method in accordance with claim 1, where the metathesis is effected with sodium hexafluoroantimonate.

* * * * *